(12) United States Patent
Bonnefous

(10) Patent No.: US 6,561,981 B2
(45) Date of Patent: May 13, 2003

(54) ULTRASONIC METHOD AND SYSTEM FOR SHEAR WAVE PARAMETER ESTIMATION

(75) Inventor: Odile Bonnefous, Nogent-sur-Marne (FR)

(73) Assignee: Koninklijke Philips Electronics N.V., Eindhoven (NL)

( * ) Notice: Subject to any disclaimer, the term of this patent is extended or adjusted under 35 U.S.C. 154(b) by 15 days.

(21) Appl. No.: 09/840,201

(22) Filed: Apr. 23, 2001

(65) Prior Publication Data

US 2002/0010398 A1 Jan. 24, 2002

(30) Foreign Application Priority Data

Apr. 26, 2000 (EP) .............................. 00401153

(51) Int. Cl.$^7$ ................................ A61B 8/00
(52) U.S. Cl. ........................ 600/443; 600/438
(58) Field of Search ........................ 600/437–472; 73/585–602

(56) References Cited

U.S. PATENT DOCUMENTS

| | | | | |
|---|---|---|---|---|
| 4,653,505 A | * | 3/1987 | Iinuma | 600/437 |
| 4,947,851 A | * | 8/1990 | Sarvazyan et al. | 600/438 |
| 5,606,971 A | * | 3/1997 | Sarvazyan | 600/438 |
| 5,810,731 A | * | 9/1998 | Sarvazyan et al. | 600/438 |

OTHER PUBLICATIONS

Yamakoshi, Y., Sato, J., and Sato, T., Ultrasonic Imaging of Internal Vibration of Soft Tissue under Forced Vibration, IEEE Transactions on Ultrasonics, Ferroelctrics, and Frequency Control, vol. 37, No. 2, Mar. 1990, p. 45–53.*

* cited by examiner

Primary Examiner—Francis J. Jaworski
Assistant Examiner—William C. Jung
(74) Attorney, Agent, or Firm—John Vodopia

(57) ABSTRACT

The invention relates to an ultrasonic diagnostic imaging method for determining propagation parameters of transient shear wave front, comprising steps of forming transient shear waves in a tissue (5), acquiring ultrasonic image data (S,S*) of the tissue, along image lines (l), during a time delay ($T_{SW}$) for a transient shear wave front to propagate over a depth (z) in said tissue, estimating the tissue velocity (V) for each line, constructing a tissue velocity image sequence [I(V)] from the ultrasonic data (S,S*) and the tissue velocities (V) on the lines, and deriving the velocities ($C_{SW}$) of the shear wave front at instants of the sequence. Tissue parameters such as elasticity are then calculated from said front velocity. The invention also relates to an ultrasonic diagnostic imaging system having processing means (100, PROCESSING1, PROCESSING2) for carrying out this method. The processing means may be a computer program product having instruction to this end.

15 Claims, 4 Drawing Sheets

ULTRASONIC METHOD AND SYSTEM FOR SHEAR WAVE PARAMETER ESTIMATION

FIELD OF THE INVENTION

The invention relates to a an ultrasonic method and an ultrasonic system for determining local propagation velocity of transient shear waves in a tissue, for displaying a sequence of velocity images of the transient shear waves and for determining tissue elasticity information.

The invention finds its application in using this information as a tool to diagnose abnormalities, such as tumors or edemas, in a patient tissue. These abnormalities are known to show changes of their mechanical properties with respect to sound background tissue. Shear wave propagation information permits of localizing said abnormalities.

BACKGROUND OF THE INVENTION

A method for determining tissue elasticity in various parts of a body is already known from Sarvazyan, U.S. Pat. No. 5,606,971. According to this known method, ultrasonic waves are focussed at different location of a tissue, using a focused ultrasonic source that transmits said ultrasonic waves to its focal region. The focused ultrasonic source is preferably an ultrasound transducer of the phased array kind. Said focussed ultrasonic waves are amplitude modulated for generating shear waves at said different locations of the tissue. Said shear waves are further detected by measuring their amplitude and phase on the surface of the tissue. At least one propagation parameter of the shear waves in the tissue is determined from the phase and amplitude measures such as shear wave velocity, attenuation coefficient, amplitude and velocity of shear displacement of tissue particles in the propagating shear wave. A calculation, based on these measures, is performed and at least one mechanical parameter of tissue is determined such as the shear elasticity modules, Young modulus, dynamic shear viscosity, using known relations. The steps of the method are repeated for all amplitude modulated focused ultrasound waves, which are focused at said various locations. The calculated values of dynamic shear viscosity and elasticity modulus are displayed in function of the coordinates of said locations.

This known method of producing shear waves necessitates the use of focussed ultrasonic sources such as phased array transducers, for transmitting a great amount of ultrasonic energy to the locations where shear waves are produced in the tissue. Focussed ultrasonic sources may have destructive effects on the patient tissue due to the necessary amount of ultrasonic energy that is locally applied.

SUMMARY OF THE INVENTION

The present invention has for an object to provide a method, and a system to carry out the method, which do not use a focused ultrasonic source, in order to avoid possible secondary effects in the patient tissue. According to the invention, shear waves are generated in a tissue using an external mechanical vibration source. The shear waves produce displacements of tissue particles. According to the invention, a standard ultrasonic diagnostic system measures the velocity of the tissue particles and the velocity of the front of the shear waves. This ultrasonic diagnostic system also has means to display a sequence of images of the shear wave front propagation.

A problem is that the shear waves propagate at about 1 m. per s. over several centimeters in the tissue, for instance 4 cm. In this case, the propagation time is about 40 ms (milliseconds). This velocity is much too high and the propagation time delay much too small to permit of visualizing the effect of shear waves on the tissue using a standard sequence of ultrasonic images produced by a standard ultrasonic diagnostic imaging system. The image frame rate of such a system is not adapted to visualizing the shear wave propagation because it is of the order of 15 images per second whereas an image frame rate of about 1 image per ms (1000 images per second) is needed for shear wave visualization.

The present invention provides, as claimed in claim 1, an ultrasonic diagnostic imaging method for determining propagation parameters of transient shear wave front, comprising steps of forming transient shear waves in a tissue, acquiring ultrasonic image data (S,S*) of the tissue, along image lines, during a time delay for a transient shear wave front to propagate over a depth (z) in said tissue, estimating the tissue velocity (V) for each line, constructing a tissue velocity image sequence [I(V)] from the ultrasonic data (S,S*) and the tissue velocities (V) on the lines, and deriving the velocities ($C_{SW}$) of the shear wave front at instants of the sequence. The invention also provides an ultrasonic diagnostic imaging method, as claimed in claim 7, for determining tissue local mechanical parameters of a tissue from the transient shear wave front velocity ($C_{SW}$).

The present invention further provides a system, as claimed in claim 8 for carrying out said methods.

The invention allows the visualization of sequences of tissue moving under the influence of shear wave, using a standard ultrasound diagnostic imaging system with a standard transducer emitting and receiving standard ultrasound and echo signals respectively. The invention further allows the localization of tissue regions having contrasting mechanical properties with respect to a background, and the determination of the mechanical parameters of said tissue regions.

BRIEF DESCRIPTION OF THE DRAWINGS

The invention is described in detail thereafter in connection with the schematic drawings in which.

DETAILED DESCRIPTION

Figure 1A:
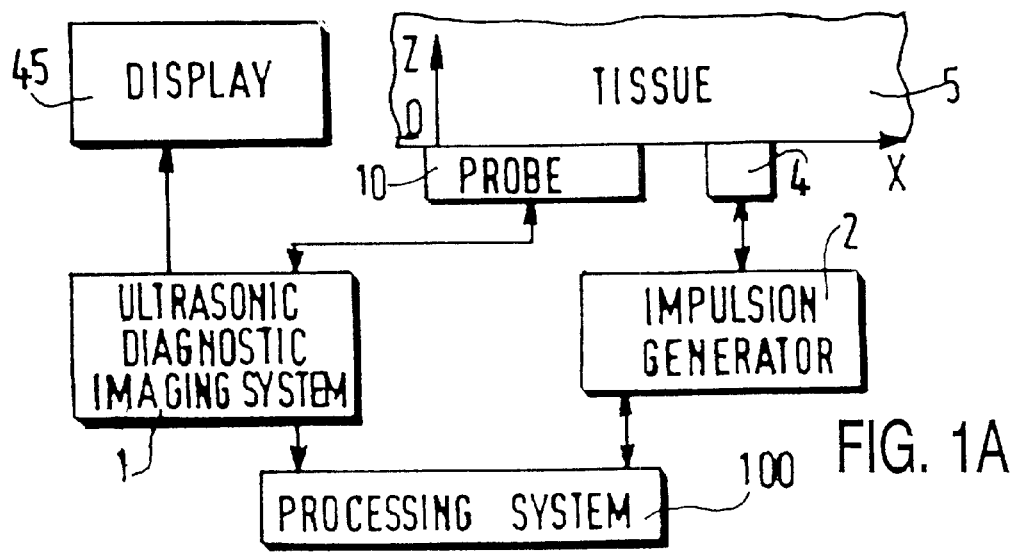
FIG. 1A is a block diagram of an ultrasonic diagnostic imaging system having means for producing shear waves in a tissue, for processing echo signals and displaying corresponding images.

FIG. 1A shows a block diagram representing a standard ultrasonic diagnostic imaging system 1 connected to a transducer 10 denoted probe and to a vibration generator 2. The ultrasonic diagnostic system is connected to a processing system 100 for the determination of local propagation velocity of transient shear waves, for the display of a sequence of images the transient shear wave front and for the determination of tissue parameters such as tissue elasticity.

Figure 1B:
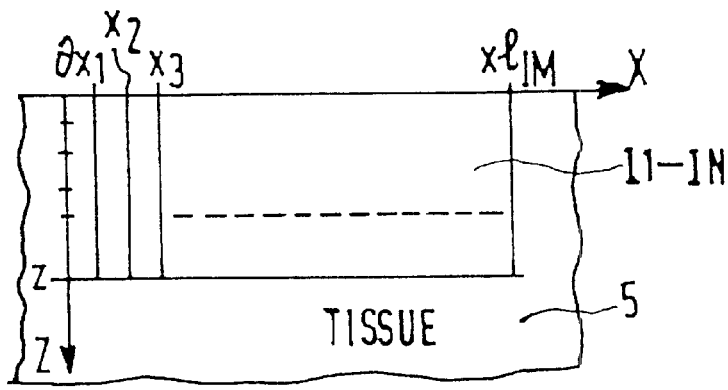
FIG. 1B illustrates the scanning of ultrasonic lines in one image.

Referring to FIG. 1B, the probe 10 is positioned in ultrasonic contact with a tissue 5 to be examined and emits ultrasonic pulses through said tissue. The probe comprises transducer elements disposed in an arrangement parallel to the surface of the tissue and to an axis OX, denoted X-axis. The transducer elements permit of emitting several ultrasonic beams of ultrasonic pulses parallel to an axis OZ denoted Z-axis, orthogonal to the X-axis. The total number $l_{IM}$ of ultrasonic beams may be for example $l_{IM}$=128 or $l_{IM}$=256. Each beam is hereafter referred to as an ultrasonic line parallel to the Z-axis and has an abscissa on the X-axis from $x_1$ to $xl_{IM}$. As the ultrasonic pulses propagate through the tissue 5, along one line, at an abscissa $x_i$ with the index i such as $1 \leq i \leq l_{IM}$, corresponding echoes are generated by tissue particles encountered along said line. These echoes are received by the probe at instants that are function of the depth z of the echo formation on said line parallel to the Z-axis. The combination of all echoes generated from reflection along one line at an abscissa $x_i$ forms a line of ultrasonic data of the tissue, which data are complex data and are denoted S and S*. The scanning of one line over a depth z of about 4 cm takes a time of less than or about Tl=100 µs; for the simplicity of explanation, it is supposed thereafter that this time is Tl=100 µs. The scanning of the $l_{IM}$ lines is performed one line after the other and forms a full 2-D image of ultrasonic data (S and S*), referred to as ultrasonic image, which ultrasonic image comprises $l_{IM}$ lines (128 or 256 lines) parallel to the Z-axis disposed at regular intervals $(x_1, x_2, \ldots xl_{IM})$. The lines are about 4 cm long measured along the Z-axis. With the hypothesis set above, it takes about a time $T_{IM}=l_{IM}100$ µs to form one 2-D ultrasonic image over a depth of 4 cm:

$T_{IM}$=12,8 ms for one ultrasonic image of 128 lines, or $T_{IM}$=25,6 ms for one ultrasonic image of 256 lines.

Referring to FIG. 1A, the ultrasonic diagnostic imaging system 1 is connected to a vibration generator 2 that is an external mechanical pulse generator 2. This external mechanical pulse generator presents the advantages of being very armless for the patient and very easy to use for the practitioner. Each mechanical pulse is applied to the tissue 5 by means of a contact body 4 and generates shear waves that propagates in tissue 5 over a depth z of about 4 cm at a velocity that has been A PRIORI estimated and that is:

$C_{SW}$=about 1 m/s

With this estimated velocity $C_{SW}$, the shear waves propagates in the tissue over said depth of 4 cm taking a time that is about:

$T_{SW}$=40 ms.

The invention proposes a method and a system for the visualization of the transient shear wave front on a display 45 connected to the standard ultrasonic diagnostic system 1. To that end, the ultrasonic diagnostic system of FIG. 1A comprises the processing system 100 associated to the standard ultrasonic diagnostic system 1, to the vibration generator 2 and to the probe 10. The probe 10 may be positioned with respect to the vibration generator 2 in any way appropriate for the standard ultrasonic diagnostic system 1 to form ultrasonic images of the tissue region 5 where the shear wave propagate.

Figure 1C:
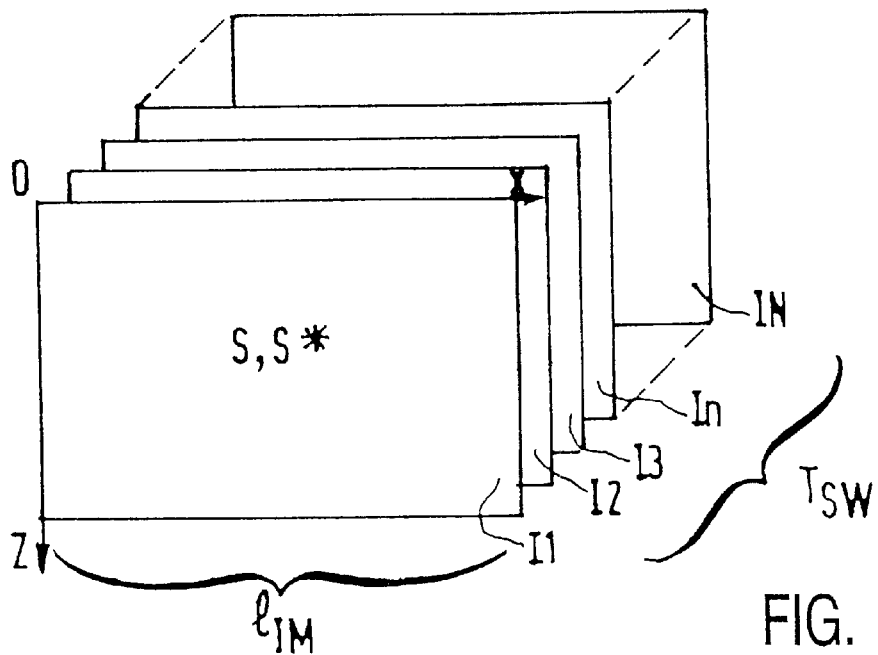
FIG. 1C illustrates the formation of an ultrasonic full-image sequence.

For visualizing the transient shear wave front, first a temporal sequence of ultrasonic images is formed during the time delay of the shear wave front propagation. Referring to FIG. 1C, for visualizing correctly this propagation, it is proposed to form a temporal sequence of a number N of ultrasonic images, for instance N=10 to 50 images. In an example described thereafter, it is chosen to form a temporal sequence of:

N=40 ultrasonic images denoted $I_1$, $I_2$ to $I_N$ regularly acquired during the time delay:

$T_{SW}$=40 ms.

So, with the previous hypothesis related to scanning time Tl of one line, the ultrasonic diagnostic imaging system must supply one ultrasonic image every 1 ms to allow the visualization of the shear wave, whereas the standard ultrasonic diagnostic imaging system is able to supply only one ultrasonic image every 12,8 ms or every 25,6 ms, which is the time $T_{IM}$. So, such a standard ultrasonic diagnostic system is not adapted to supply an image frame rate appropriate to construct the temporal ultrasonic image sequence that is required to visualize the transient shear wave front propagation. The processing system 100 permits of solving this problem.

Figure 2:
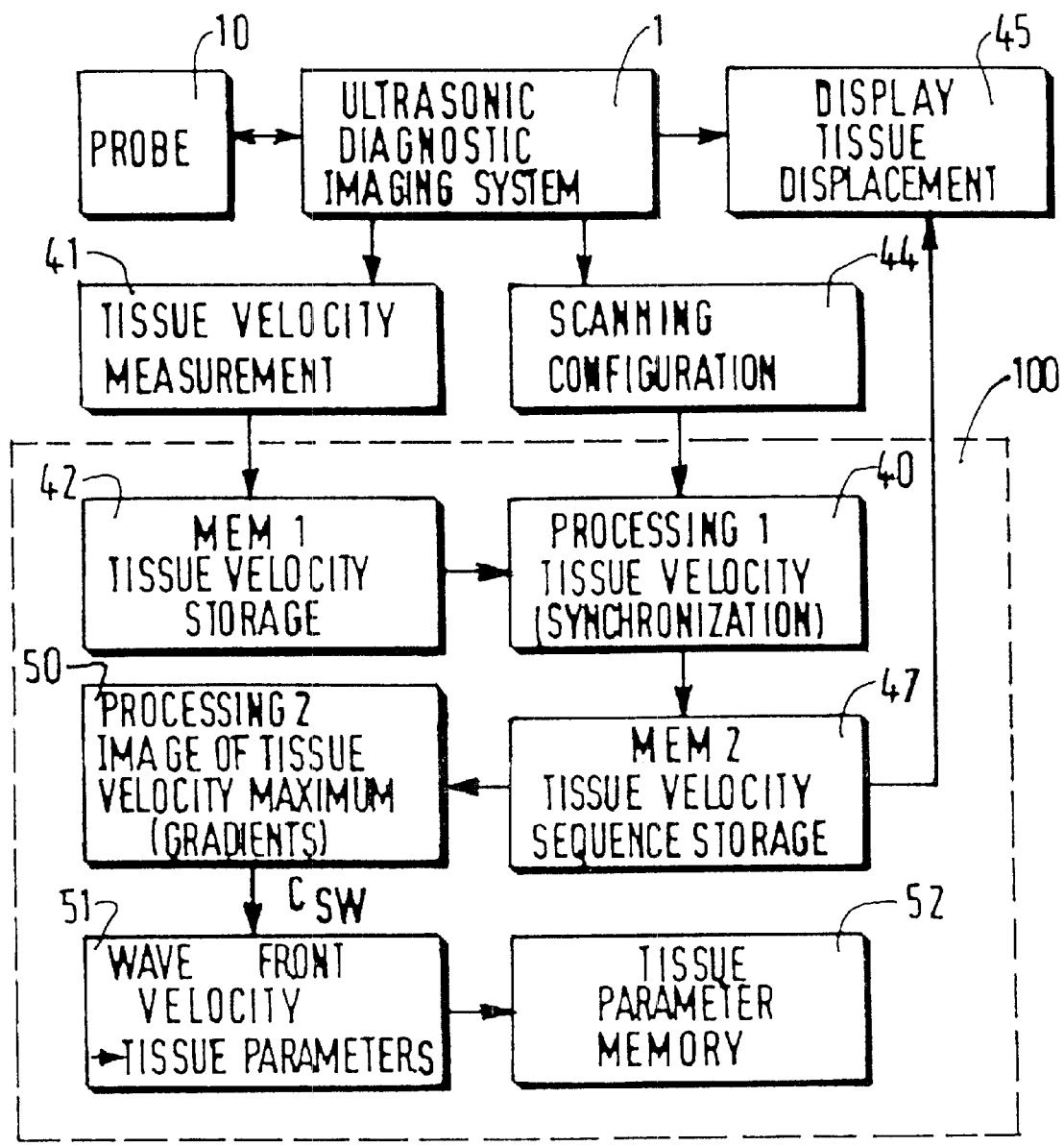
FIG. 2 is a block diagram of an ultrasonic diagnostic imaging system for processing ultrasonic signals of a tissue region under the influence of shear wave, for measuring the wave front velocity, and tissue mechanical local parameters.

FIG. 2 shows a block diagram representing the system 100 having processing means for acquiring sequences of temporal ultrasonic sub-images, for estimating the local velocity of tissue particles under the action of the shear waves, for constructing a sequence of tissue velocity full-images, for estimating the shear wave front velocity and for visualizing the displacement of tissue under the influence of the transient shear wave propagation.

Figure 3A:
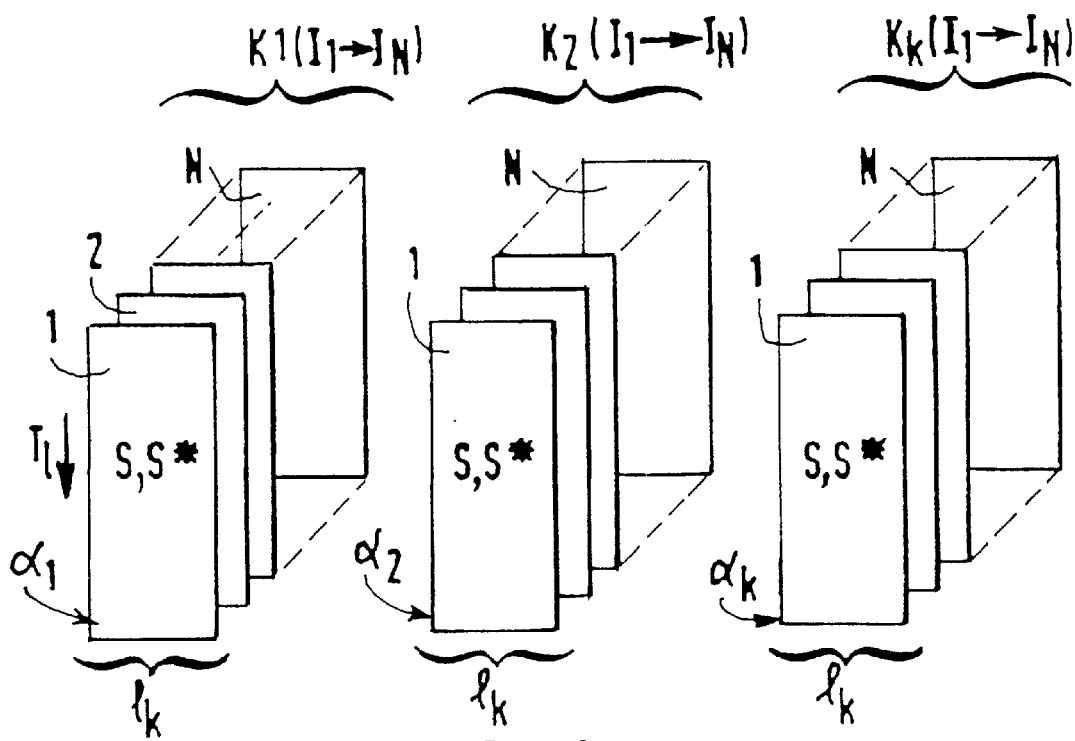
FIGS. 3A and 3B illustrate respectively the formation of sequences of ultrasonic sub-images and the formation of corresponding sequences of tissue velocity sub-images.

Referring to FIG. 3A, at a first instant $\alpha_1$, the vibration generator generates a first shear wave in the tissue 5, and, using the scanning configuration 44 of the ultrasonic diagnostic system 1, at the same instant $\alpha_1$, the probe 10 that is coupled to tissue 5 begins scanning a first line at the abscissa $x_1$ in order to provide a first line of ultrasonic data denoted S and S*. It takes Tl=100 µs to the system to scan one line, and said system disposes of $T_{SW}$=40 ms to scan 4 cm, over which the shear wave propagates, and must supply N=40 temporal ultrasonic images at the rate of 1 ultrasonic image per ms. So, the system has time to scan a number $1 < l_K \leq 10$ adjacent lines of the first ultrasonic image $I_1$, disposed at abscissa $x_1, x_2, \ldots x_{10}$, thus forming a first band of lines of ultrasonic data (S and S*), which band is denoted $K_1(I_1)$ in said first ultrasonic image $I_1$. For example, $l_K$=10 lines.

Referring to FIG. 3A, the system further scans a number $l_K$=10 adjacent lines of the second temporal ultrasonic image $I_2$, disposed at the same abscissa $x_1, x_2, \ldots x_{10}$, thus forming a first band of lines of ultrasonic data (S and S*), denoted $K_1(I_2)$ of $l_K$=10 lines at the same abscissa in the second ultrasonic image $I_2$.

Referring to FIG. 3A, the system further scans $l_K=10$ adjacent lines of each temporal ultrasonic image including $I_{40}$, forming in each temporal ultrasonic image $I_1$ to $I_{40}$ only one band $K_1$ of $l_K=10$ lines disposed at the abscissa $x_1$ to $x_{10}$. The first band $K_1$ is denoted first sub-image $K_1$ of each completed ultrasonic image of 128 or 256 lines to be performed. It takes $T_{SW}=40$ ms for the system to perform N=40 temporal ultrasonic sub-images $K_1(I_1)$ to $K_1(I_{40})$ of ultrasonic data S and S*. This forms a first sequence of ultrasonic sub-images of the ultrasonic data (S and S*).

As it may be understood of those skilled in the art, the number of lines of the ultrasonic sub-image is calculated: by determining the total number $l_{SW}$ of lines that are possibly scanned during the time propagation $T_{SW}$ of the shear wave, knowing the time Tl for scanning one line, by fixing the number N of ultrasonic images of the sequence that is appropriate to visualize the shear wave front displacement, which gives the number $l_K$ of lines possibly scanned per ultrasonic image, from $I_1$ to $I_N$, during the time of one pulse of the vibration generator 2:

$l_K=l_{SW}/N$

At a second instant $\alpha_2$, the vibration generator 2 generates a second shear wave in the same region of tissue 5, and, using the scanning configuration 44, at the same instant $\alpha_2$, the probe 10, that is coupled to tissue 5, begins scanning a first line at the abscissa $x_{11}$, which forms the first line of ultrasonic data (S and S*) of a second band $K_2(I_1)$ of the first temporal ultrasonic image $I_1$. So, now, the system scans $l_K=10$ lines at the abscissa $x_{11}$ to $x_{20}$, thus forming the second band of ultrasonic data (S and S*), which band is denoted $K_2(I_1)$ and is composed of $l_K=10$ lines in the first temporal ultrasonic image $I_1$.

Then as previously described in reference to FIG. 3A, the system further scans $l_K=10$ adjacent lines of each temporal ultrasonic image $I_1$ to $I_{40}$, disposed at the abscissa $x_{11}$ to $x_{20}$, forming the bands of temporal ultrasonic sub-images $K_2(I_1)$ to $K_2(I_{40})$.

At further instants $\alpha_3$ to $\alpha_k$, the vibration generator 2 provides a mechanical pulse that generates a shear wave propagating in the same region of tissue 5 and, using the scanning configuration 44, at the same instant, the probe 10 that is coupled to the tissue 5 begins scanning a first line of $l_K=10$ lines to form the ultrasonic image of a corresponding band K of the temporal ultrasonic images $I_1$ to $I_{40}$.

This scanning operation is performed until a number k of bands or ultrasonic sub-images $K_1$ to $K_k$ are constructed for each ultrasonic image $I_1$ to $I_{40}$. The number k of ultrasonic sub-images and the number $l_K$ of lines in each ultrasonic sub-images are chosen appropriately by the user in function of the number of lines $l_{IM}$ n of each full image. At the instant $\alpha_k$, the last sequence of ultrasonic sub-images is constructed.

Referring to FIG. 2, the ultrasonic data of the sequences of ultrasonic sub-images are used to construct corresponding sequences of tissue velocity sub-images. The velocities of tissue particles under the action of shear waves are measured along each scanning line of the ultrasonic sub-image sequence. The measure of velocity of displacement of tissue is an operation well known of those skilled in the art, which is usually performed using the standard ultrasonic system 1 that has means 41 for tissue velocity measurement.

The ultrasonic diagnostic imaging system 1 may perform the tissue velocity measurement on each scanning line at the abscissae $x_1$ to $xl$ of the ultrasonic sub-images of the sequences respectively $K_1$ to $K_k$ using different methods. A known method is for example the "phase shift method" according to which the tissue velocity [V(n,l,z)] is supplied by the processing means 41, from the ultrasonic data S and S* of the lines of the sequences of ultrasonic sub-images, according to the formula:

$$V(n, l, z) = \frac{C}{4\pi(l_K T_l fo)} Arg \sum_{m=n-p}^{m=n+p} S(m, l, z)S*(m+1, l, z)$$

where n is the image number in the sequence of N ultrasonic sub-images, with $1 \leq n \leq N-1$, where l is the line number in the considered ultrasonic sub-image among the $l_K$ total number of lines in said ultrasonic sub-image $K_1$ to $K_k$ of a given ultrasonic sub-image n in which the velocity of tissue is estimated, Tl is the scanning time of one line, fo is the mean frequency of the echo signal, S and S* are the values of the complex ultrasonic signals, z is the depth of the point where the velocity is estimated and C is the velocity of ultrasounds in the tissue (in the present example, $1 \leq n \leq 39$, $l_K=10$ and Tl=100 µs). In the above formula, p is the number of data that are averaged in order to calculate the velocity; p may be taken equal to 2 for example; m is calculated from n and p.

Figure 3B:
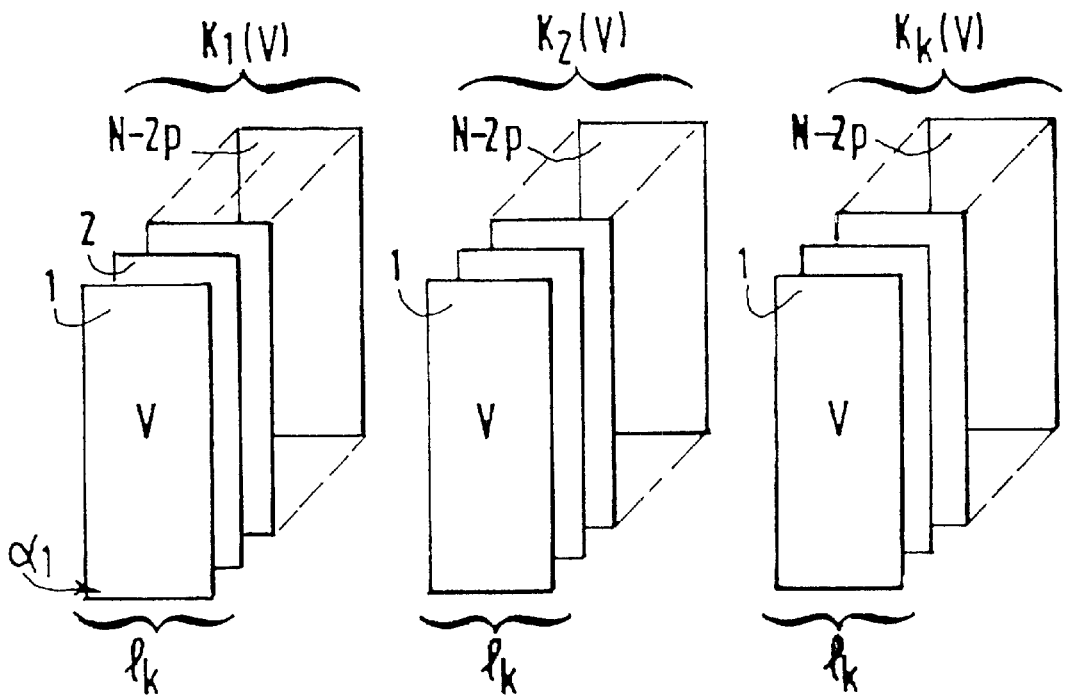

Referring to FIG. 3B, with this method, sequences of tissue velocity sub-images are constructed, that are composed of a number N−2p (for example N−2p=40−4=36) of sub-images, which is different from the number N of sub-images (N=40) of the sequences of ultrasonic sub-images. However the number k of sequences of tissue velocity sub-images is the same as the number of sequences of ultrasonic sub-images.

In a variant, the tissue velocity may be measured by a well known "temporal shift method", or other methods that are the choice of the user.

Then, the sequences of tissue velocity sub-images are stored in a first memory means 42, denoted MEM1, and notably the tissue velocity values are stored as a function of their locations, denoted P(x,z,t) where x is the abscissa of the scanning line along the X-axis, t is the instant, which is different from n, corresponding to said image number n and z is the depth along the Z-axis. So P(x,z,t) is a point in a tissue velocity sub-image at an instant t corresponding to n at the abscissa x and depth z, and in a sub-image $K_1[V(n,l,z)]$ to $K_k[V(n,l,z)]$ of the k sequences of (N−2p) tissue velocity sub-images.

Referring to FIG. 2, the k tissue velocity sub-images $K_1[V(n,l,z)]$ to $K_k([V(n,l,z)]$ are further processed in order to be assembled for constructing a temporal sequence of N−2p tissue velocity full-images, denoted $I_1[V(n,l,z)]$ to $I_{N-2p}[V(n,z)]$.

This operation is performed using a first processing means 40 denoted PROCESSING1 of the processing system 100. The PROCESSING1 operates a synchronization of the lines of all tissue velocity sub-images for forming tissue velocity full-images. In this operation, all the first lines of all the k tissue velocity first sub-images, which are adjacent, are synchronized to the first line of the first sub-image formed at the first instant $\alpha_1$, in order to cover a first full-image, and all the lines of all the k tissue velocity sub-images corresponding to said given full-image are synchronized on said first line, taking into account the time delay between the formation of each image line. Then, all the adjacent sub-images of the tissue velocity sequences are processed in the same way with respect to the instant of formation of the first sub-images among the adjacent sub-images, for covering tissue velocity full-images.

Figure 4:
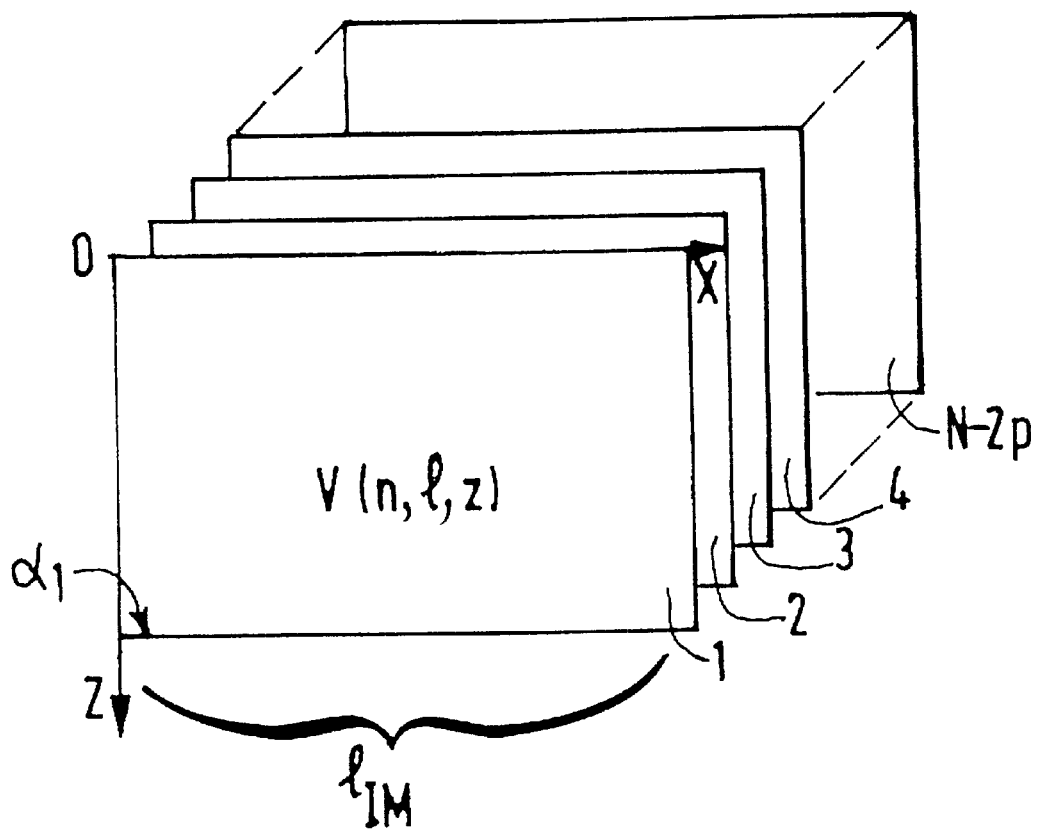
FIG. 4 illustrates the construction of a sequence of tissue velocity full-images.

Referring to FIG. 4, the resulting tissue velocity sequence is then constituted by the number N−2p=36 tissue velocity full-images $I_1[V(n,l,z)]$ to $I_{N-2p}[V(n,l,z)]$ that are so constructed. By this operation of synchronization, each tissue velocity full-image $I_1[V(n,l)]$ to $I_{N-2p}[V(n,l)]$ of the tissue velocity sequence corresponds to a respective instant t of shear wave propagation in the tissue, t being function of n previously defined.

In order to perform the synchronization operation, the velocity values related to the lines, which are stored in MEM1 are extracted and input to the synchronization means PROCESSING1, which has for a function to correct the time delay produced by the scanning operation. First, in order to construct one full-image at one instant t of the tissue velocity sequence, the lines of each tissue velocity sub-image of the k tissue velocity sequences must be synchronized to the first line of the first tissue velocity sub-image corresponding to said tissue velocity full-image. Second, the point on the lines of said full-image must be synchronized to corresponding tissue velocity values estimated from the sequences of tissue velocity sub-images, taking into account that the sequences of ultrasonic sub-images comprise N ultrasonic sub-images presented at instants n whereas the sequences of tissue velocity sub-images comprise N−2p tissue velocity sub-images presented at instants t. It is to be noted that the real time delay between instants tl and $tl_{+1}$ corresponding to the velocities on two adjacent lines at the same depth z, respectively V(n,l,z) and V(n,l+1,z), is Tl, which is the time delay for scanning one line. It is also to be noted that the time necessary to scan one ultrasonic sub-image is $l_K$Tl. So, the time delay between the instants t1 and tl corresponding to the velocities V(n,1,z) and V(n,l,z) is:

tl−t1=(l−1)Tl.

For the above-described reasons, finding the actual velocity on a given line numbered l in the tissue velocity sub-image is performed by using an interpolation function, denoted I, of the velocity data in function of time t, according to the formula:

fl(t)=I[V(n,l,z)] from n=p to N−2p
where
t=[n+(l−1)]l that is smaller than $l_K$Tl.

This function fl (t) is a filtering function applied on the velocity data that provides the actual tissue velocity on a considered line of the tissue velocity image to be constructed. This filtering function may be of a kind that is known by those skilled in the art, for example a cubic spline function or a sinus cardinal function.

The number k of sub-images K, the number N of temporal ultrasonic images and the number l of lines to form a temporal ultrasonic image are the choice of the user. At the end of this phase 3, a temporal sequence of a number N−2p=40−2p of tissue velocity full-images has been constructed from the k acquired sequences of N ultrasonic sub-images and the estimation of the tissue velocity.

Referring to FIG. 2, the data issued of PROCESSING1 are stored in a second memory means 47 denoted MEM2.

The full-images are tissue velocity images of the region 5 where the shear waves propagate, and are displayed in sequence using the display means 45 of system 1. At this stage of the process, the display shows the tissue regions moving under the action of the mechanical pulse supplied by the vibration generator 2.

Referring to FIG. 2, in a further phase, the data of the tissue velocity image sequence are extracted from MEM2 and supplied to a second processing means 50, denoted PROCESSING2. From the data of the tissue velocity sequence, which comprise the tissue velocity values at each point of each image, and at each instant t of the shear wave propagation, one further image, referred to as $I_{MAX}$, is constructed in PROCESSING2.

Figure 5:
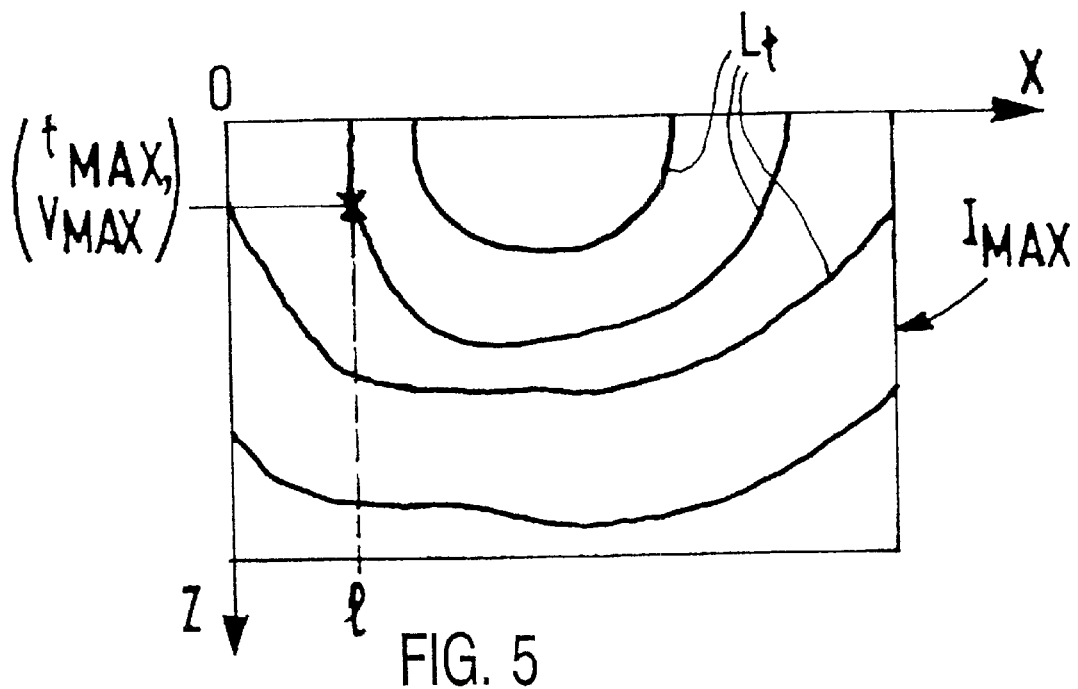
FIG. 5 illustrates an image constructed from the tissue velocity full-image sequence to provide the shear wave front velocity measure.

Referring to FIG. 5, in PROCESSING2, this new image $I_{MAX}$, called image of the maximum velocities, is build by writing, at points on lines of said image, the instants, referred to as $t_{MAX}$, among $t_1$ to $t_{N-2p}$, when the velocities of the tissue are maximum, denoted $V_{MAX}$. The different points of the image $I_{MAX}$ that correspond to maximum of tissue velocities at the same instant $t_{MAX}$ are joined by lines denoted $L_t$: all the points on a same line are points of maximum velocities for a same instant t: the lines are equal-levels of velocities. So, these lines show the instants of propagation of the shear wave front. The estimation of the gradients of time in this image $I_{MAX}$ permits of determining the velocity of said shear wave front. The wave front velocity, denoted $C_{SW}$ is estimated in PROCESSING2, in function of the gradients in said new image $I_{MAX}$, by the following formula:

$$C_{SW} = \left( \frac{dt^2_{MAX}}{dx} + \frac{dt^2_{MAX}}{dz} \right)^{-\frac{1}{2}}$$

The propagation front velocity data extracted from PROCESSING2 are further processed in a calculation means 51 for estimating the tissue parameters such as for example the elasticity of tissue regions from formulae known of the document cited in the introductory part. The tissue parameters are stored in memory means 52 in order to be further used as diagnostic tools for helping to the diagnostic of tumors or other diseases.

This ultrasonic diagnostic imaging system may be a standard ultrasonic apparatus 1,10 associated to a processing means 100 comprising a suitably programmed computer, a processor of a workstation, or a special purpose processor having circuit means such as LUTs, Memories, Filters, Logic Operators, that are arranged to perform the functions of the method steps according to the invention. The workstation may also comprise a keyboard, a screen 45 and a mouse. The processing system may be connected to supplementary storing means to store medical images.

What is claimed is:
1. An ultrasonic diagnostic imaging method for determining propagation parameters of a transient shear wave front, comprising:
    forming transient shear waves in a tissue;
    acquiring ultrasonic image data (S,S*) of the tissue, along ultrasonic image lines (l), during a time delay ($T_{SW}$) for a transient shear wave front to propagate over a depth (z) in said tissue;

estimating a tissue velocity (V) for each line;

constructing a tissue velocity image sequence [I(V)] from the ultrasonic image data (S,S*) and the tissue velocities (V) on the lines; and deriving velocities ($C_{SW}$) of the shear wave front at instants of the tissue velocity image sequence.

2. The method as claimed in claim 1, wherein acquiring ultrasonic image data includes:

estimating the time delay ($T_{SW}$) for a transient shear wave to propagate over a given depth (z) of tissue, calculating the number of scan lines ($l_{SW}$) that can be ultrasonically scanned during said time delay, setting a predetermined number (N) of full-images for an ultrasonic full-image sequence, each ultrasonic full-image comprising a predetermined number of scan lines ($l_{IM}$), calculating the number of lines ($l_K$) that can be possibly scanned in each full-image of the ultrasonic image sequence, estimating a number (k) of adjacent sub-images ($K_k$) in each ultrasonic full-image, each sub-image being formed of said number of possibly scanned lines ($l_K$), in order to cover each full-image of the sequence by the estimated number of adjacent sub-images, and determining an ultrasonic scanning configuration for scanning the corresponding sub-images of the sequence images with as many sequences of sub-images as the estimated number of adjacent sub-images.

3. The method as claimed in claim 2, wherein acquiring ultrasonic image data further includes:

scanning the tissue according to the scanning configuration while initiating one shear wave each time one sequence of ultrasonic sub-images is started.

4. The method as claimed in claim 3, wherein estimating tissue velocity and constructing the sequence of tissue velocity images includes:

estimating the tissue velocities (V) on the scan lines from the ultrasonic data (S,S*) as a function of the number of lines ($l_K$) in the ultrasonic sub-images and as a function of the image number (n) of the sub-image in the sequences of ultrasonic sub-images, forming sequences of tissue velocity sub-images [K(V)] corresponding to the sequences of ultrasonic sub-images [K(I)], considering the adjacent sub-images appropriate to cover respectively full-images in order to construct one sequence of velocity full-images [I(V)] during the propagation of one shear wave, and synchronizing the lines of the adjacent tissue velocity sub-images, relating to each full-image, with the first line of the corresponding sub-image of the first sequence for forming said sequence of velocity full-images.

5. The method as claimed in claim 4, wherein deriving the shear wave front velocities includes:

in the sequence of tissue velocity images [I(V)], determining points, on the image lines, for which the tissue velocities are maximum ($V_{MAX}$) as a function of the instant ($t_{MAX}$) of formation of the considered tissue velocity image, from said tissue velocity image sequence, forming a further image, referred to as image ($I_{MAX}$) of the maximum velocities, which image is formed of points having respectively the locations on said image lines and being attributed the values of the instants ($t_{MAX}$) for which the tissue velocities ($V_{MAX}$) are maximum in said tissue velocity image sequence, and linking the points having the same instant values for forming an image of the transient shear wave fronts at said instant values.

6. The method as claimed in claim 5, wherein deriving the shear wave front velocities further includes:

in said image of the maximum velocity ($t_{MAX}$, $V_{MAX}$), determining time gradient values as a function of image point locations (x,z), and estimating the transient shear wave front velocities ($C_{SW}$) from the gradient values of said image of the maximum.

7. An ultrasonic diagnostic imaging method for determining mechanical parameters of a tissue by the determination of propagation parameters of a transient shear wave front, comprising:

estimating transient shear wave front velocities ($C_{SW}$) according to the method of claim 1; and estimating tissue local mechanical parameters from the transient shear wave front velocities.

8. A computer program product comprising a set of instructions for carrying out a method as claimed claim 1.

9. An ultrasonic diagnostic imaging system, for determining mechanical parameters of a tissue by the determination of propagation parameters of a transient shear wave front, comprising:

a vibration generator for producing transient shear waves in a tissue using external mechanical pulses; and an ultrasonic imaging system configured for acquiring ultrasonic data (S, S*) of the tissue, along ultrasonic image lines, during a time delay ($T_{SW}$) for a transient shear wave front to propagate over a depth (z) in said tissue, and for estimating tissue velocities for each line, the ultrasonic imaging system further including a processing system having:

a first processing means for constructing a tissue velocity image sequence from the ultrasonic data and the tissue velocities on the lines, a second processing means for deriving velocities of the shear wave front at instants of the sequence, and a calculating means for estimating tissue local mechanical parameters from the transient shear wave front velocities ($C_{SW}$).

10. The system as claimed in claim 9, wherein said ultrasonic imaging system is further configured for acquiring image data via a scanning configuration means adapted for:

estimating the time delay ($T_{SW}$) for a transient shear wave to propagate over a given depth of tissue, calculating the number of scan lines that can be ultrasonically scanned during said time delay, setting a predetermined number (N) of full-images for an ultrasonic full-image sequence, each ultrasonic full-image comprising a predetermined number ($l_{IM}$) of scan lines, calculating the number ($l_K$) of lines that can be possibly scanned in every full-image of the ultrasonic image sequence, estimating a number (k) of sub-images in each ultrasonic full-image, each sub-image being formed of said number of possibly scanned lines, in order to cover each full-image of the sequence by the estimated number of adjacent sub-images, and wherein the scanning configuration means is further for scanning the tissue so that corresponding ultrasonic sub-images of the sequence images are scanned with as many sequences of ultrasonic sub-images as the estimated number of adjacent ultrasonic sub-images, and so that one sequence of ultrasonic sub-images is started each time one shear wave is initiated.

11. The system as claimed in claim 10, further comprising: velocity measurement means for estimating the tissue velocities on the scan lines from the ultrasonic data, as a function of the number of lines in the ultrasonic sub-images and as a function of the number of images in the sequences of ultrasonic sub-images, and for forming sequences of tissue velocity sub-images corresponding to the sequences of ultrasonic sub-images.

12. The system as claimed in claim 11, wherein the first processing means receives the sequences of tissue velocity images, processes the adjacent sub-images appropriate to cover respective full-images in order to construct one sequence of velocity full-images during the propagation of one shear wave, by synchronizing the lines of the adjacent tissue velocity sub-images relating to each full-image with the first line of the corresponding sub-image of the first sequence for forming said sequence of tissue velocity full-images.

13. The system as claimed in claim 11, wherein the second processing means receives the sequence of tissue velocity full-images, determines points, on the image lines, for which the tissue velocities are maximum in function of the instant of formation of a considered tissue velocity image, forms a further image, referred to as image of the maximum, which image is formed of points having respectively the locations on said image lines and being attributed the values of the instants for which the tissue velocities are maximum in said tissue velocity image sequence, and links the points having the same instant values for forming an image of the transient shear wave fronts at said instant values.

14. The system as claimed in claim 9, further comprising display means for displaying the sequence of tissue velocity images and the images of the transient shear wave front propagation.

15. An apparatus comprising:

means to acquire medical ultrasonic data;

a system, having access to said medical ultrasonic data, to process the data as claimed in claim 9; and means for displaying the processed images.

* * * * *